United States Patent
Bassler et al.

(10) Patent No.: US 7,527,712 B2
(45) Date of Patent: May 5, 2009

(54) METHOD FOR THE CONTINUOUS PURIFICATION BY DISTILLATION OF THE SOLVENT METHANOL, USED IN THE SYNTHESIS OF PROPYLENE OXIDE

(75) Inventors: Peter Bassler, Viernheim (DE); Hans-Georg Goebbel, Kallstadt (DE); Joaquim Henrique Teles, Otterstadt (DE); Peter Rudolf, Ladenburg (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 674 days.

(21) Appl. No.: 10/521,784

(22) PCT Filed: Jul. 22, 2003

(86) PCT No.: PCT/EP03/07986

§ 371 (c)(1), (2), (4) Date: Jan. 21, 2005

(87) PCT Pub. No.: WO2004/009566

PCT Pub. Date: Jan. 29, 2004

(65) Prior Publication Data
US 2005/0258026 A1   Nov. 24, 2005

(30) Foreign Application Priority Data
Jul. 23, 2002   (DE) ................ 102 33 388

(51) Int. Cl.
*B01D 3/14* (2006.01)
*C07C 27/28* (2006.01)
*C07C 29/80* (2006.01)

(52) U.S. Cl. .............. 203/29; 203/71; 203/79; 203/99; 203/DIG. 19; 203/DIG. 23; 568/913

(58) Field of Classification Search ............ 203/29, 203/71, 79, 99, 100, DIG. 19, DIG. 23; 568/909.8, 568/913
See application file for complete search history.

(56) References Cited

U.S. PATENT DOCUMENTS 2,471,134 A   5/1949   Wright
4,230,533 A   10/1980  Giroux (Continued)

FOREIGN PATENT DOCUMENTS

DE   196 23 609   12/1997

(Continued)

OTHER PUBLICATIONS

Kaibel, Gerd. "Distillation Columns with Vertical Partitions", Chem. Eng. Technol., vol. 10, pp. 92-98, 1987.

(Continued)

*Primary Examiner*—Virginia Manoharan
(74) *Attorney, Agent, or Firm*—Oblon, Spivak, McClelland, Maier & Neustadt, P.C.

(57) ABSTRACT

Process for the continuously operated purification by distillation of the methanol used as solvent in the synthesis of propylene oxide by reaction of a hydroperoxide with propylene, with the methoxypropanols being separated off simultaneously, wherein the solvent mixture obtained in the synthesis is separated in a dividing wall column into a low-boiling fraction including methanol, an intermediate-boiling fraction containing the methoxypropanols as azeotrope with water and a high-boiling fraction including water and propylene glycol.

9 Claims, 5 Drawing Sheets

U.S. PATENT DOCUMENTS

| | | | | |
|---|---|---|---|---|
| 6,881,853 | B2* | 4/2005 | Teles et al. | 549/531 |
| 6,958,111 | B2* | 10/2005 | Rust et al. | 202/158 |
| 7,323,579 | B2* | 1/2008 | Gobbel et al. | 549/541 |

FOREIGN PATENT DOCUMENTS

| | | |
|---|---|---|
| DE | 197 23 949 | 12/1998 |
| EP | 0 122 367 | 10/1984 |
| EP | 0 126 288 | 11/1984 |
| EP | 0 133 510 | 2/1985 |
| EP | 1 127 601 | 8/2001 |
| WO | 00/07965 | 2/2000 |
| WO | 02/02544 | 1/2002 |
| WO | 02/45811 | 6/2002 |

OTHER PUBLICATIONS

Kaibel, Gerd et al. "Gestaltung destillativer Trennungen unter Einbeziehung thermodynamischer Gesichtspunkte", Chem.-Ing.-Tech., vol. 61, No. 1, pp. 16-25, with English abstract 1989.

Kaibel, G. et al. "Thermodynamics—guideline for the development of distillation column arrangements", Gas Separation & Purification, vol. 4, pp. 109-114 1990.

"Distillation's great leap forward?" Process Engineering, vol. 2, pp. 33-34 1993.

Lestak, F. et al. "Heat Transfer Across the Wall of Dividing Wall Columns", Trans IChemE, vol. 72, part A, pp. 639-644 1994.

Lestak, Frigyes et al. "Advanced Distillation Saves Energy & Capital", Chemical Engineering, vol. 7, pp. 72-76 1997.

"Production", Hydrogen Peroxide, Ullmann's Encyclopedia of Industrial Chemistry, $5^{th}$ ed., vol. 13, pp. 447-456.

* cited by examiner

METHOD FOR THE CONTINUOUS PURIFICATION BY DISTILLATION OF THE SOLVENT METHANOL, USED IN THE SYNTHESIS OF PROPYLENE OXIDE

The present invention relates to a continuously operated process for the purification by distillation of the methanol used as solvent in the synthesis of propylene oxide by reaction of a hydroperoxide with propylene, with the methoxypropanols and the high boilers being separated off simultaneously using a dividing wall column. The solvent mixture obtained in the synthesis is separated into a low-boiling fraction comprising methanol, an intermediate-boiling fraction comprising the methoxypropanols as azeotrope with water and a high-boiling fraction comprising water. In a particular embodiment, the dividing wall column can also be in the form of two thermally coupled columns.

In the customary processes of the prior art, propylene oxide can be obtained by reaction of propylene with hydroperoxides in one or more stages.

For example, the multistage process described in WO 00/07965 provides for the reaction to comprise at least the steps (i) to (iii):
 (i) reaction of the hydroperoxide with propylene to give a product mixture comprising propylene oxide and unreacted hydroperoxide,
 (ii) separation of the unreacted hydroperoxide from the mixture resulting from step (i),
 (iii) reaction of the hydroperoxide which has been separated off in step (ii) with propylene.

Accordingly, the reaction of propylene with the hydroperoxide takes place in at least two steps (i) and (iii), with the hydroperoxide separated off in step (ii) being reused in the reaction.

The reactions in steps (i) and (iii) are carried out in two separate reactors which are preferably configured as fixed-bed reactors. It is advantageous to carry out step (i) under substantially isothermal reaction conditions and step (iii) under adiabatic reaction conditions. It is likewise advantageous for the reaction to be heterogeneously catalyzed.

This reaction sequence is preferably carried out in a solvent and the hydroperoxide used is preferably hydrogen peroxide. The particularly preferred solvent is methanol.

Here, the hydrogen peroxide conversion in step (i) is from about 85% to 90% and that in step (iii) is about 95% based on step (ii). Over both steps, the total hydrogen peroxide conversion is about 99% at a propylene oxide selectivity of about 94-95%.

Owing to the high selectivity of the reaction, this process is also referred to as the coproduct-free synthesis of propylene oxide.

The propylene oxide has to be separated off from a mixture comprising methanol as solvent, water, hydrogen peroxide as hydroperoxide and also by-products. By-products are, for example, the methoxypropanols, viz. 1-methoxy-2-propanol and 2-methoxy-1-propanol, which are formed by reaction of propylene oxide with methanol. Propylene glycols, hydroperoxypropanols, acetaldehydes and methyl formate are also present in the mixture.

Methoxypropanols can be used, for example, as solvents in surface coating systems. In the work-up, they are obtained in a stream comprising the methoxypropanols together with methanol, water and propylene glycol.

The separation processes carried out for recovering these materials of value have hitherto typically been carried out in distillation columns having a side offtake or in columns connected in series. This procedure is costly because it has an increased energy requirement and requires complicated apparatus.

It is an object of the present invention to optimize the purification by distillation of the methanol used as solvent in the preferably coproduct-free synthesis of propylene oxide by reaction of a hydroperoxide with propylene, so that the methoxypropanols are recovered simultaneously and the otherwise usual energy requirement is reduced. The solvent should be obtained in a quality which enables it to be reused for the abovementioned synthesis of propylene oxide.

Figure 1:
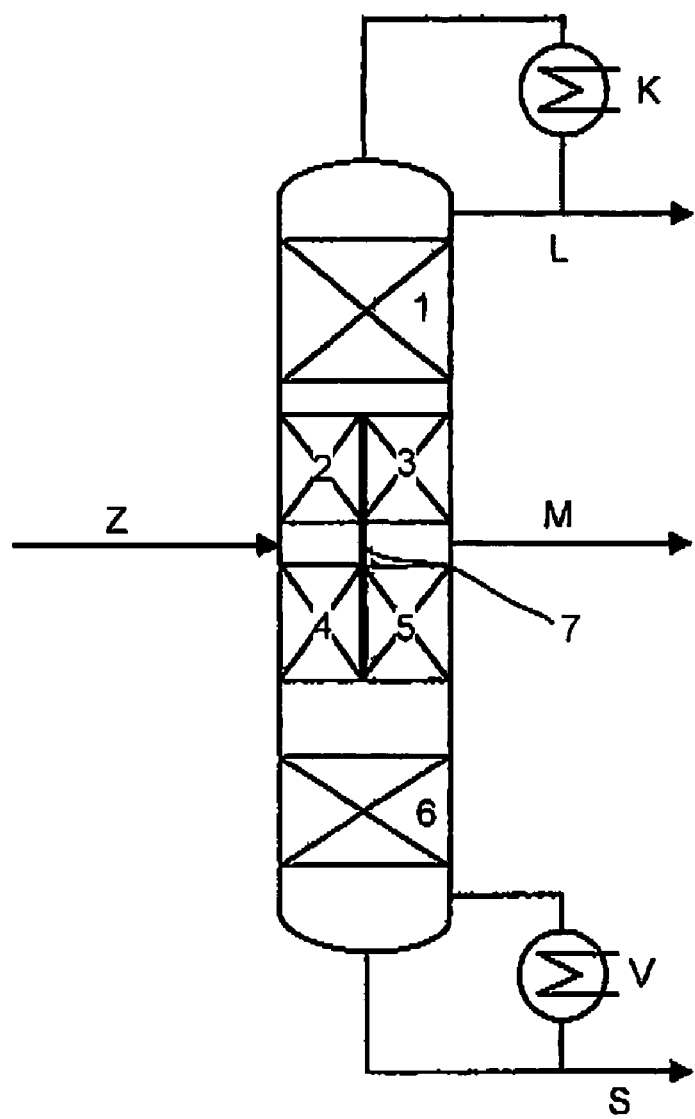
FIG. 1 shows the purification of methanol used as a solvent in the synthesis of propylene oxide.

We have found that this object is achieved by a continuously operated process for the purification of the methanol used as solvent and the methoxypropanols formed in the preferably coproduct-free synthesis of propylene oxide by reaction of a hydroperoxide with propylene by distillation in a dividing wall column.

The present invention accordingly provides a process for the continuously operated purification by distillation of the methanol used as solvent in the synthesis of propylene oxide by reaction of a hydroperoxide with propylene, with the methoxypropanols being separated off simultaneously, wherein the solvent mixture obtained in the synthesis is separated in a dividing wall column into a low-boiling fraction comprising methanol, intermediate boiling fraction comprising the methoxypropanols as azeotrope with water and a high-boiling fraction comprising water and propylene glycol.

According to the present invention, the methanol is distilled off via the top of the column, the methoxypropanols are taken off as azeotrope with water via the side offtake and the high boilers are taken off at the bottom of the dividing wall column.

The process of the present invention enables the methanol to be obtained in sufficiently pure form for it to be able to be reused, for example, for the synthesis of propylene oxide. The methoxypropanols, too, are obtained in good purity as an azeotropic mixture with water. Compared to the processes disclosed in the prior art, the novel process of the present invention leads to a reduced outlay in terms of apparatus. Furthermore, the dividing wall column has a particularly low energy consumption and thus offers advantages in terms of the energy requirement over a conventional column or an assembly of conventional columns. This is highly advantageous for industrial use.

Distillation columns having side offtakes and a dividing wall, hereinafter also referred to as dividing wall columns, are known. They represent a further development of distillation columns which have only one side offtake but no dividing wall. The use of the last-named type of column is restricted because the products taken off at the side offtake are never completely pure. In the case of products taken off at the side offtake in the enrichment section of the column, which are usually taken off in liquid form, the side product still contains proportions of low-boiling components which should be separated via the top. In the case of products taken off at the side offtake in the stripping section of the column, which are usually taken off in gaseous form, the side product still contains proportions of high boilers. The use of conventional side offtake columns is therefore restricted to cases in which contaminated side products are permissible.

However, when a dividing wall is installed in such a column, the separation action can be improved. This type of construction mes it possible for side products to be taken off in pure form. A dividing wall is installed in the middle region above and below the feed point and the side offtake. This can be fixed in place by welding or can be merely pushed into place. It seals off the offtake section from the inflow section and prevents crossmixing of liquid and vapor streams over the entire colt cross section in this part of the column.

This reduces the total number of distillation columns required in the fractionation of multicomponent mixtures whose components have similar boiling points.

This type of column has been used, for example, for the separation of an initial mixture of the components methane, ethane, propane and butane (U.S. Pat. No. 2,471,134), for the separation of a mixture of benzene, toluene and xylene (U.S. Pat. No. 4,230,533) and for the separation of a mixture of n-hexane, n-heptane and n-octane (EP 0 122 367).

Dividing wall columns can also be used successfully for separating mixtures which boil azeotropically (EP 0 133 510).

Finally, dividing wall columns in which chemical reactions can be carried out with simultaneous distillation of the products are also known. Examples which may be mentioned are esterifications, transesterifications, saponifications and acetalizations (EP 0 126 288).

FIG. 1 schematically shows the purification of the methanol used as solvent in the synthesis of propylene oxide by distillation in a dividing wall column having a side offtake, with the methoxypropanols and the high boilers being separated off simultaneously.

Here, the solvent mixture resulting from the synthesis of propylene oxide is introduced continuously as feed Z into the dividing wall column. In the column, this mixture is separated into the low-boiling fraction L comprising methanol the intermediate-boiling fraction M comprising the methoxypropanols as azeotrope with water and the high-boiling fraction S comprising water.

The low-boiling fraction L is taken off at the top of the column and condensed by means of the condenser K. At the side offtake for intermediate boilers M, the methoxypropanols are taken off as azeotrope with water in liquid or gaseous form. To take off the product at the side offtake, it is possible to use receivers in which the liquid or condensing vapor can be collected and which may be located either inside or outside the column. The high-boiling fraction S is taken off at the bottom of the column. Energy is introduced via the vaporizer V.

The process of the present invention is carried out using a dividing wall column which preferably has from 15 to 60, more preferably from 20 to 35, theoretical plates. The process of the present invention can be carried out particularly advantageously using such a design.

In a preferred embodiment of the process of the present invention, therefore, the dividing wall column has from 15 to 60 theoretical plates.

The upper, combined region 1 of the inflow and offtake part of the dividing wall column preferably has from 5 to 50%, more preferably from 15 to 30%, of the total number of theoretical plates in the column, the enrichment section 2 of the inflow part preferably has from 5 to 50%, more preferably from 15 to 30%, the stripping section 4 of the inflow part preferably has from 5 to 50%, more preferably from 15 to 30%, the stripping section 3 of the offtake part preferably has from 5 to 50%, more preferably from 15 to 30%, the enrichment section 5 of the offtake part preferably has from 5 to 50%, more preferably from 15 to 30%, and the common lower region 6 of the inflow and offtake part of the dividing wall column preferably has from 5 to 50%, more preferably from 15 to 30%, in each case of the total number of theoretical plates in the column. The dividing wall 7 prevents miring of liquid and vapor streams.

The sum of the number of theoretical plates in the regions 2 and 4 in the inflow part is preferably from 80 to 110%, more preferably from 90 to 100%, of the sum of the number of theoretical plates in the regions 3 and 5 in the ode part.

It is likewise advantageous for the feed point and the side offtake to be arranged at different heights in the column relative to the position of the theoretical plates. The feed point is preferably located at a position which is from 1 to 8, more preferably from 3 to 5, theoretical plates above or below the side offtake.

The dividing wall column used in the process of the present invention is preferably configured either as a packed column containing random packing or ordered packing or as a tray column. For example, it is possible to use sheet metal or mesh packing having a specific surface area of from 100 to 1 000 $m^2/m^3$, preferably from about 250 to 750 $m^2/m^3$. Such packing provides a high separation efficiency combined with a low pressure drop per theoretical plate.

In the abovementioned configuration of the column, the region of the column divided by the dividing wall, which consists of the enrichment section 2 of the inflow part, the stripping section 3 of the offtake part, the stripping section 4 of the offtake part and the enrichment section 5, or parts thereof, is/are preferably provided with ordered packing or random packing and the dividing wall 7 is thermally insulated in these regions.

The solvent etude to be separated is introduced continuously into the column in the form of the feed stream Z which comprises the low boilers, intermediate boilers and high boilers.

This feed stream is generally liquid. However, it can be advantageous to subject the feed steam to preliminary vaporization and subsequently introduce it into the column as a two-phase, i.e. gaseous and liquid, mixture or in the form of one gaseous stream and one liquid stream. This preliminary vaporization is particularly useful when the feed stream contains relatively large amounts of low boilers. The preliminary vaporization enables a considerable load to be taken off the stripping section of the column.

The feed stream is advantageously metered by means of a pump or via a static inflow head of at least 1 m into the inflow part. This inflow is preferably introduced via a cascade regulation in combination with the regulation of the liquid level should be nothing here in the receiver of the inflow part. The regulation is set so that the amount of liquid introduced into the enrichment section 2 cannot drop below 30% of the normal value. It has been found that such a procedure is important to even out troublesome fluctuations in the amount or concentration of the feed.

It is likewise important that the division of the liquid flowing down from the stripping section 3 of the offtake part of the column between the side offtake and the enrichment section 5 of the offtake part is set by means of a regulation device so that the amount of liquid going to the region 5 cannot drop below 30% of the normal value.

Adherence to these prerequisites has to be ensured by means of appropriate regulation methods.

Regulation mechanisms for the operation of dividing wall columns have been described, for example, in Chem. Eng. Technol. 10 (1987) 92-98, Chem,-Ing.-Technol. 61 (1989), No. 1, 16-25, Gas Separation and Purification 4 (1990) 109-114, Process Engineering 2 (1993) 33-34, Trans IChemE 72 (1994) Part A 639-644, Chemical Engineering 7 (1997) 72-76. The regulation mechanisms described in this prior art can also be employed for or applied to the process of the present invention.

The regulation principle described below has, been found to be particularly useful for the continuously operated purification of the solvent by distillation. It is readily able to cope with fluctuations in loading. The distillate is thus preferably taken off under temperature control.

A temperature regulation device which utilizes the downflow quantity, the reflux ratio or preferably the quantity of runback as regulating parameter is provided in the upper section 1 of the column. The measurement point for the temperature regulation is preferably located from three to eight, more preferably from four to six, theoretical plates below the upper end of the column.

Appropriate setting of the temperature then results in the liquid flowing down from the section 1 of the column being divided at the upper end of the dividing wall 7 so that the ratio of the liquid flowing to the inflow part to that flowing to the offtake part is preferably from 0.1 to 1,0, more preferably from 0.3 to 0.6.

In this method, the downflowing liquid is preferably collected in a receiver which is located in or outside the column and from which the liquid is then fed continuously into the column. This receiver can thus take on the task of a pump reservoir or provide a sufficiently high static head of liquid which makes it possible for the liquid to be passed on further in a regulated manner by means of regulating devices, for example valves. When packed columns are used, the liquid is firstly collected in collectors and from there conveyed to an internal or external receiver.

The vapor stream at the lower end of the dividing wall 7 is set by selection add/or dimensioning of the separation internals and/or incorporation of pressure-reducing devices, for example orifice plates, so that the ratio of the vapor stream in the inflow part to that in the offtake part is preferably from 0.8 to 1.2, preferably from 0.9 to 1.1.

In the abovementioned regulation principle, at temperature regulation device which utilizes the quantity taken off at the bottom as regulating parameter is provided in the lower combined section 6 of the column. The bottom product can therefore be taken off under temperature control. The measurement point for the temperature regulation device is preferably located from three to six, more preferably from four to six, theoretical plates above the lower end of the column.

In addition, the level regulation in column section 6 (bottom of the column) can be utilized for regulating the quantity taken off at the side offtake. For this purpose, the liquid level in the vaporizer is used as regulating parameter.

The differential pressure over the column can also be utilized as regulating parameter for the heating power. The distillation is advantageously carried out at a pressure at the top of from 1 to 15 bar, preferably from 5 to 13 bar. Accordingly, the heating power of the vaporizer at the bottom of the column is selected to maintain this pressure range.

This results in a distillation temperature which is preferably in the range from 30 to 140° C., more preferably from 60 to 140° C. and in particular from 100 to 130° C. The distillation temperature is measured at the top of the column.

Accordingly, a preferred embodiment of the process of the present invention provides for the pressure to be from 1 to 15 bar and the distillation temperature to be from 30 to 140° C., in each case measured at the top of the column.

To be able to operate the dividing wall column in a trouble-free manner, the abovementioned regulation mechanisms are usually employed in combination.

In the separation of multicomponent mixtures into low-boiling, intermediate-bowling and high-boiling fractions, there are usually specifications in respect of the maximum permissible proportion of low boilers and high boilers in the intermediate-boiling fraction. Here, individual components which are critical to the separation problem, referred to as key components, or else the sum of a plurality of key components are/is specified.

Adherence to the specification for the high boilers in the intermediate-boiling fraction is preferably regulated via the division ratio of the liquid at the upper end of the dividing wall 7. The division ratio is set so that the concentration of key components for the high-boiling fraction in the liquid at the upper end of the dividing wall amounts to from 10 to 80% by weight, preferably from 30 to 50% by weight, of the value which is to be achieved in the streams taken off at the side. The liquid division can then be set so that when the concentration of key components of the high-boiling fraction is higher, more liquid is introduced into the inflow section, and when the concentration of key components is lower, less liquid is introduced into the inflow section.

Accordingly, the specification for the low boilers in the intermediate-boiling fraction is regulated by means of the heating power. Herb, the heating power in the vaporizer is set so that the concentration of key components for the low-boiling fraction in the liquid at the lower end of the dividing wall amounts to from 10 to 80% by weight, preferably from 30 to 50% by weight, of the value which is to be achieved in the products taken off at the side. Thus, the heating power is set so that when the concentration of key components of the low-boiling fraction is higher, the heating power is increased, and when the concentration of key components of the low-boiling fraction is lower, the heating power is reduced.

The concentration of low and high boilers in the intermediate-boiling fraction can be determined by customary analytical methods. For example, infrared spectroscopy can be used for detection, with the compounds present in the reaction mixture being identified by means of their characteristic absorptions. These measurements can be carried out in-line directly in the column. However, preference is given to using gas-chromatographic methods. In this case, sampling facilities are then provided at the upper and lower end of the dividing wall. Liquid or gaseous samples can then be taken continuously or at intervals from the column and analyzed to determine their compositions. The appropriate regulation mechanisms can then be activated as a function of the composition.

An objective of the process of the present invention is to provide methanol and the methoxypropanols as azeotrope with water in a purity of preferably at least 95%.

In a specific embodiment of the dividing wall column, it is also possible for the inflow part and the offtake part which are separated from one another by the dividing wall 7 not to be present in one column but to be physically separate from one another. In this specific embodiment, the dividing wall column can thus comprise at least two physically separate columns which then have to be thermally coupled with one another.

In a preferred embodiment of the process of the present invention, therefore, the dividing wall column is configured as two thermally coupled columns.

Such thermally coupled columns generally exchange vapor and liquid between them. However, in specific embodiments, they can also be operated in such a way that they only exchange liquid. This specific embodiment has the advantage that the thermally coupled columns can also be operated under different pressures, which can make it possible to achieve better setting of the temperature level required for the distillation than in the case of a conventional dividing wall column.

In general, these thermally coupled columns are operated so that the low-boiling fraction and the high-boiling fraction are taken off from different columns. The operating pressure of the column from which the low-boiling fraction is taken is preferably from about 0.5 to 3 bar higher than the pressure in the column from which the high-boiling fraction is taken.

Furthermore, in the case of coupled columns it can also be advantageous to vaporize bottom streams partly or completely in an additional vaporizer and only then pass them to the next column. This prevaporization is particularly useful when the bottom stream from the first column contains relatively large amounts of intermediate boilers. In this case, the prevaporization can be carried out at a lower temperature level and some of the load is taken from the vaporizer of the second column, if this column is equipped with a vaporizer. This measure also significantly decreases the load on the stripping section of the second column.

The prevaporized stream can be fed to the next column either as a two-phase stream or in the form of two separate stream.

Conversely, it is also possible for low-boiling streams taken off at the top to be partly or completely condensed before they are passed to the next column. This measure, too, can contribute to better separation between low boilers and intermediate boilers present therein.

A further embodiment of the process of the present invention therefore provides for the liquid bottom stream taken from one of the coupled columns to be partly or completely vaporized before it is fed to the other column; and/or the gaseous stream taken from the top of one of the coupled columns to be partly of completely condensed before it is fed to the other column.

Examples of dividing wall columns in the specific embodiment of thermally coupled columns are shown schematically in FIGS. 2, 3, 4 and 5. According to the present invention, the low-boiling fraction L comprising methanol, the intermediate-boiling fraction M comprising the methoxypropanols as azeotrope with water and the high-boiling fraction S comprising water together with propylene glycol can be separated from one another by means of these arrangements.

Figure 2:
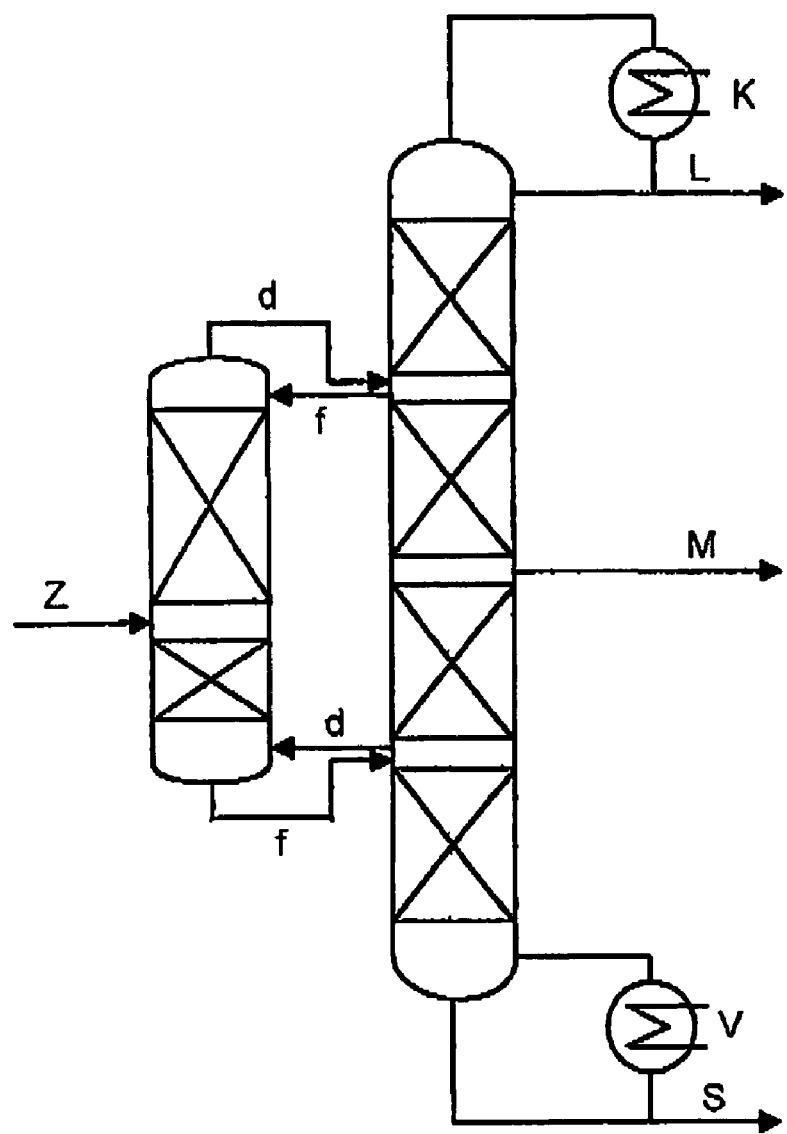
FIG. 2 shows two thermally coupled columns as dividing wall columns.

FIG. 2 shows two thermally coupled columns, in which the column into which the feed Z is introduced exchanges vapor d and liquid f with the downstream column both via the top and via the bottom. Energy is introduced essentially via the vaporizer V of the column downstream of the feed column. Here, the low-boiling fraction L can be obtained via the top of the downstream column by condensation in the condenser K, the intermediate-boiling fraction M can be obtained from the side offtake and the high-boiling fraction S can be obtained at the bottom.

Figure 3:
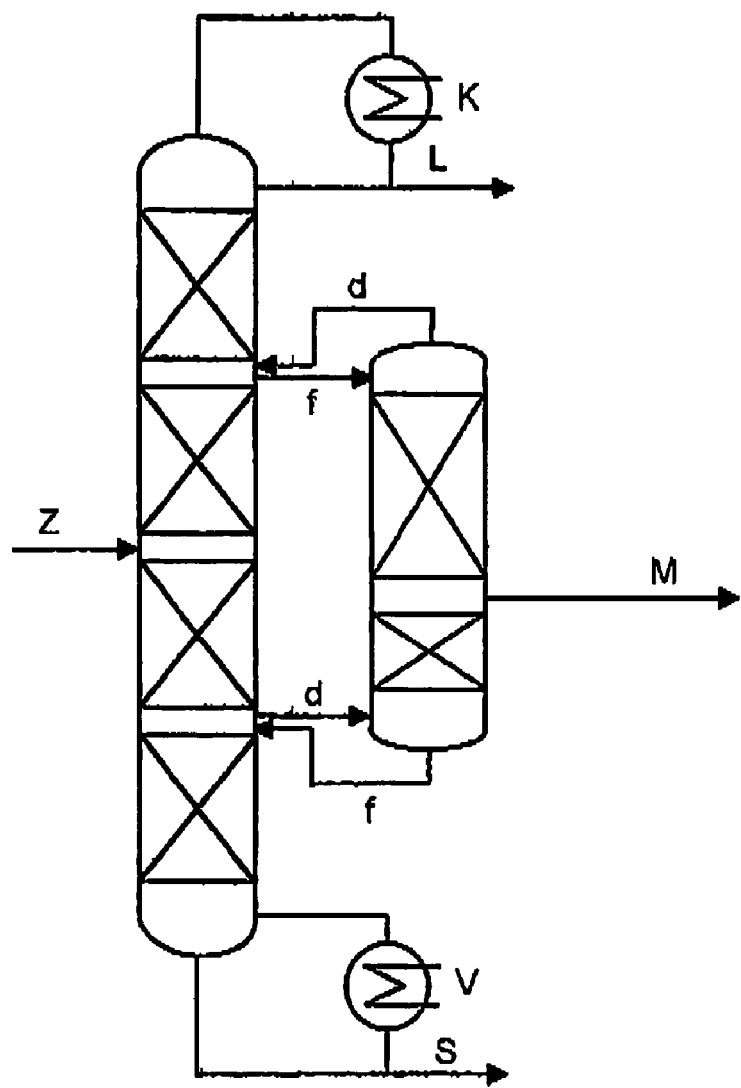
FIG. 3 shows low boiling and high boiling fractions separate in a feed column.

An arrangement as outlined in FIG. 3 is also possible. Here, the low-boiling fraction L and the high-boiling faction S are separated off in the feed column, the first via the top and the second at the bottom. The intermediate-boiling fraction M is obtained at the side offtake of the downstream column. The downstream column can exchange vapor d and liquid f with the feed column via the top and bottom, respectively. Energy is introduced essentially via the vaporizer of the feed column.

Figure 4:
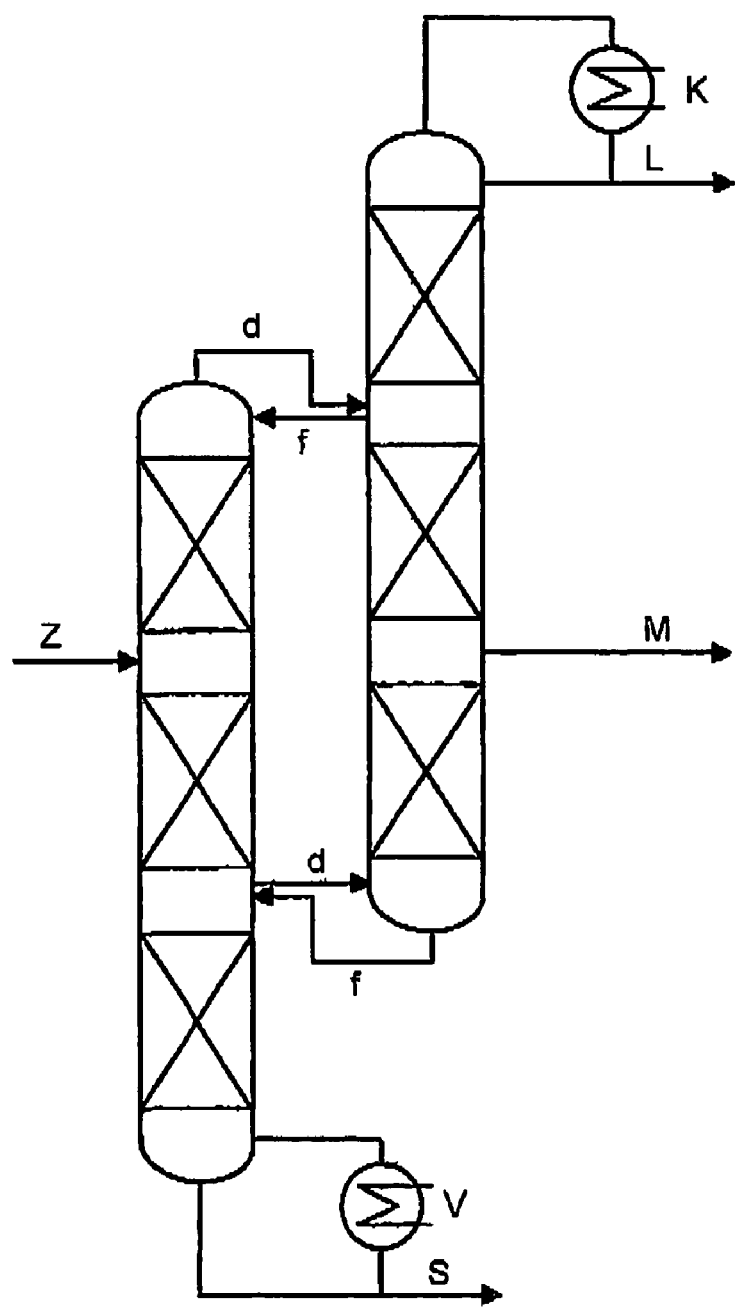
FIG. 4 shows a dividing wall column in which the high-boiling fraction is obtained at the bottom of a feed column.

FIG. 4 shows an arrangement in which the high-boiling fraction S is obtained at the bottom of the feed column. The low-boiling fraction L is obtained at the top of the downstream column and the intermediate-boiling fraction M is obtained via the side offtake of the downstream column. Energy is introduced essentially via the vaporizer of the feed column.

Figure 5:
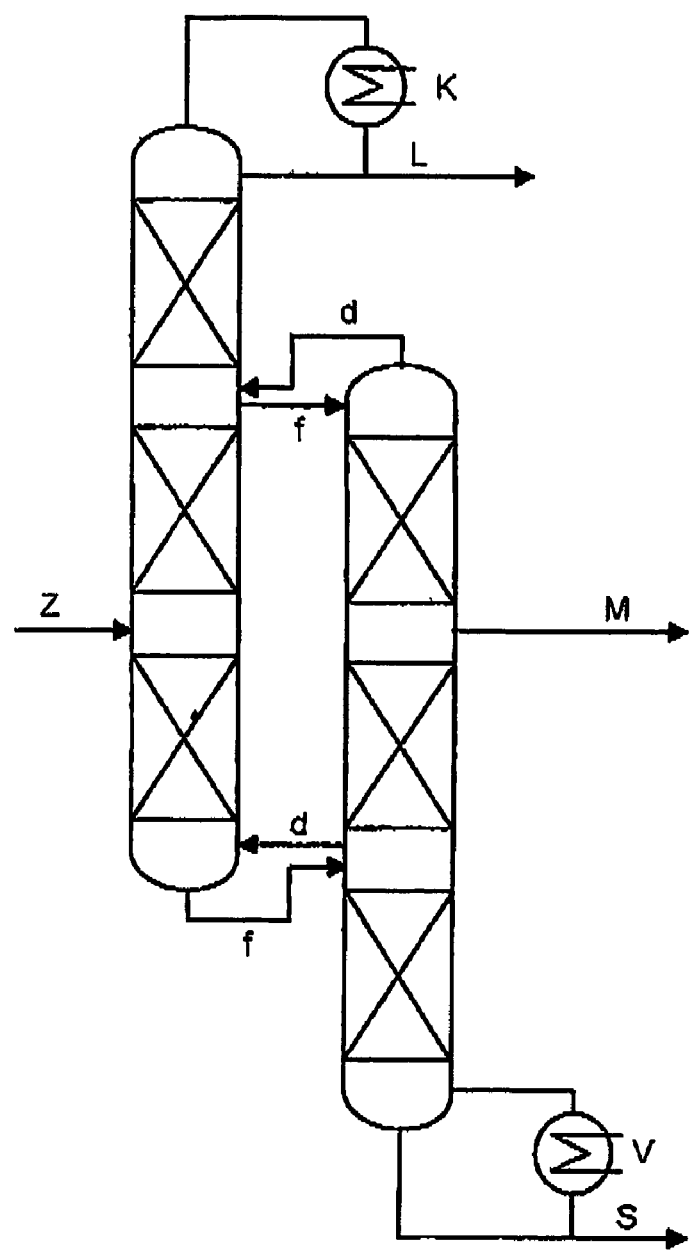
FIG. 5 shows a dividing wall column in which a low boiling fraction is obtained via the top of a feed column.

FIG. 5 shows an arrangement in which the low-boiling fraction L is obtained via the top of the feed column. In the downstream column, the high-boiling fraction S is obtained at the bottom and the intermediate-boiling fraction M is obtained via the side offtake. Energy is introduced essentially via the vaporizer of the column downstream of the feed column.

Accordingly, in another embodiment of the process of the present invention, the solvent mixture is separated into the low-boiling, intermediate-boiling and high-boiling fractions in the column downstream of the feed column, or the low-boiling and high-boiling fractions are taken off from the solvent mixture in the feed column and the intermediate-boiling fraction is taken off in the downstream column, or the high-boiling fraction is taken off from the solvent mixture in the feed column and the low-boiling and intermediate-boiling fractions are taken off in the downstream column, or the low-boiling fraction is taken off from the solvent mixture in the feed column and the intermediate-boiling and high-boiling fractions are taken off in the downstream column.

The columns of FIGS. 2 to 5 can also be configured as packed columns containing random packing or ordered packing or as tray columns. For example, sheet metal or mesh packing having a specific surface area of from 100 to 1 000 $m^2/m^3$, preferably from about 250 to 750 $m^2/n^3$, can be used as ordered packing. Such packing provides a high separation efficiency combined with a low pressure drop per theoretical plate.

The feed to the process of the present invention can be obtained from a propylene oxide synthesis using the starting materials known from the prior art.

Propylene can be used as "chemical grade" propylene. Such propylene contains propane, with propylene and propane being present in a volume ratio of from about 97:3 to 95:5.

As hydroperoxide, it is possible to use the known hydroperoxides which are suitable for the reaction of the organic compound. Samples of such hydroperoxides are tert-butyl hydroperoxide and ethylbenzene hydroperoxide. Preference is given to using hydrogen peroxide as hydroperoxide for the oxirane synthesis, with an aqueous hydrogen peroxide solution also being able to be used.

Hydrogen peroxide can be prepared, for example, by the anthraquinone process as described in "Ullmann's Encyclopedia of Industrial Chemistry", $5^{th}$ Editon, Volume 13, pages 447 to 456.

It is likewise conceivable to obtain hydrogen peroxide by converting sulfuric acid into peroxodisulfuric acid by anodic oxidation with simultaneous evolution of hydrogen at the cathode. Hydrolysis of the peroxodisulfuric acid then leads via peroxomonosulfuric acid to hydrogen peroxide and sulfuric acid, which is thus recovered.

It is of course also possible to prepare hydrogen peroxide from the elements.

The methanol used as solvent for the reaction can be used in the form of customary technical-grade product and then preferably has a purity of at least 95%.

As catalysts for the preparation of propylene oxide, preference is given to using catalysts which comprise a porous oxidic material, e.g. a zeolite. The catalysts used preferably comprise a titanium-, germanium-, tellurium-, vanadium-, chromium-, niobium- or zirconium-containing zeolite as porous oxidic material.

Specific mention may be made of titanium-, germanium-, tellurium-, vanadium-, chromium-, niobium- and zirconium-containing zeolites having a pentasil zeolite structure, in particular the types which can be assigned X-ray-crystallographically to the ABW, ACO, AEI, AEL, AEN, AET, AFG, AFI, AFN, AFO, AFR, AFS, AFT, AFX, AFY, AHT, ANA, APC, APD, AST, ATN, ATO, ATS, ATT, ATV, AWO, AWW, BEA, BIK, BOG, BPH, BRE, CAN, CAS, CFI, CGF, CGS, CHA, CHI, CLO, CON, CZP, DAC, DDR, DFO, DFT, DOH, DON, EAB, EDI EMT, EPI, ERI, ESV, EUO, FAU, FER, GIS, GME, GOO, HEU, IFR, ISV, ITE, JBW, KFI LAU, LEV, LIO, LOS, LOV, LTA, LTL, LTN, MAZ, MEI, MEL, MEP, MER, MFI, MPS, MON, MOR, MSO, MTF, MTN, MTT, MTW, MWW, NAT, NES, NON, OFF, OSI, PAR, PAU, PHI, RHO, RON, RSN, RTE, RTH, RUT, SAO, SAT, SBE, SBS, SBT, SFF, SGT, SOD, STF, STI, STT, TER, THO, TON, TSC, VET, VFI, VNI, VSV, WIE, WEN, YUG, ZON structure or to mixed structures comprising two or more of the abovementioned structures. Furthermore, titanium-containing zeolites having the ITQ-4, SSZ-24, TTM-1, UTD-1, CIT-1 or CIT-5 structure are also conceivable for use in the process of the present invention. Further titanium-containing zeolites which may be mentioned are those of the ZSM-48 or ZSM-12 structure.

Particular preference is given to Ti zeolites having an MFI or MEL structure or an MFI/MEL mixed structure. Very particular preference is given to the titanium-containing zeolite catalysts which are generally referred to as "TS-1", "TS-2", "TS-3" and also Ti zeolites having a framework structure isomorphous with β-zeolite.

It is especially advantageous to use a heterogeneous catalyst comprising the titanium-containing silicalite TS-1.

It is possible to use the porous oxidic material itself as catalyst. However, it is of course also possible for the catalyst used to be a shaped body comprising the porous oxidic material. All processes known from the prior art can be used for producing the shaped body from the porous oxidic material.

Noble metals in the form of suitable noble metal components, for example in the form of water-soluble salts, can be applied to the catalyst material before, during or after the one or more shaping steps in these processes. This method is preferably employed for producing oxidation catalysts based on titanium silicates or vanadium silicates having a zeolite structure, and it is thus possible to obtain catalysts which contain from 0.01 to 30% by weight of one or more noble metals from the group consisting of ruthenium rhodium, palladium, osmium, iridium, platinum, rhenium, gold and silver in this way. Such catalysts are described, for example, in DE-A 196 23 609.6.

Of course, the shaped bodies can be processed further. All methods of comminution are conceivable, for example splitting or crushing the shaped bodies, as are further chemical treatments as are described above by way of example.

When a shaped body or a plurality thereof is used as catalyst, it/they can, after deactivation has occurred in the process of the present invention, be regenerated by a method in which the deposits responsible for deactivation are burned off in a targeted manner. This is preferably carried out in an inert gas atmosphere containing precisely defined amounts of oxygen-donating substances. This regeneration process is described in DE-A 197 23 949.8. It is also possible to use the regeneration processes mentioned there in the discussion of the prior art.

In general, the reaction temperature for the preparation of the propylene oxide in steps (i) and (iii) is in the range from 0 to 120° C., preferably in the range from 10 to 100° C. and more preferably in the range from 20 to 90° C. The pressures which occur range from 1 to 100 bar, preferably from 1 to 40 bar, more preferably from 1 to 30 bar. Preference is given to employing pressures under which no gas phase is present.

The concentration of propylene and hydrogen peroxide in the feed steam is generally selected so that the molar ratio is preferably in the range from 0.7 to 20, more preferably in the range from 0.8 to 5.0, particularly preferably in the age from 0.9 to 2.0 and in particular in the range from 1.0 to 1.6.

The residence times in the reactor or reactors in the propylene oxide synthesis depend essentially on the desired conversions. In general, they are less than 5 hours, preferably less than 3 hours, more preferably less than 1 hour and particularly preferably about half an hour.

As reactors for the propylene oxide synthesis, it is of course possible to use all conceivable reactors which are best suited to the respective reactions. A reactor is not restricted to an individual vessel. Rather, it is also possible to use, for example, a cascade of stirred vessels.

Fixed-bed reactors are preferably used as reactors for the propylene oxide synthesis. Further preference is given to using fixed-bed tube reactors as fixed-bed reactors.

In the above-described propylene oxide synthesis which is preferably employed, particular preference is given to using an isothermal fixed-bed reactor as reactor for step (i) and an adiabatic fixed-bed reactor for step (iii), with the hydroperoxide being separated off in a separation apparatus in step (ii).

The invention is illustrated by the following example.

EXAMPLE

Propylene oxide was prepared from propylene by reaction with hydrogen peroxide using the method described in WO 00/07965, with the reaction being carried out in methanol as solvent. The solvent mixture comprising methanol and the methoxypropanols which was obtained after the propylene oxide had been separated off and was to be worked up had the following composition:

about 80.0% by weight of methanol, about 5.0% by weight of methoxypropanols an about 15.0% by weight of water and propylene glycol.

The objective of the work-up was to separate methanol and the methoxypropanols (as azeotrope with water) from one another with a very low energy consumption. The methanol was to be obtained in a purity of at least 95%.

For this purpose, the mixture was distilled with the aid of a dividing wall column having a side offtake, with methanol being taken off via the top of the column, the methoxypropanols being taken off as azeotrope with water from the side offtake and water in admixture with propylene glycol being taken off at the bottom of the column.

The energy required in the distillation was sed as a measure of the effectiveness of the separation. It was calculated as the vaporizer power divided by the throughput per unit time of the nature to be separated through the column. As column arrangements, the configurations shown in the table were selected:

| Column arrangement | Energy requirement/(kg/h) [kW/(kg/h)] | Energy saving [%] |
| --- | --- | --- |
| Conventional column with side offtake | 0.98 | — |
| Two conventional columns connected in series | 0.89 | 9.2 |
| Dividing wall column | 0.73 | 25.5 |

It can clearly be seen that the dividing wall arrangement had a considerable energy advantage compared to the conventional distillation apparatus, since the energy requited for the distillation was significantly lower than in the case of distillation using the two conventional distillation arrangements comprising the conventional column with side offtake and the two conventional columns connected in series.

The methanol obtained by distillation in the dividing wall column could be reused for the propylene oxide synthesis.

LIST OF REFERENCE NUMERALS FOR FIGS. 1 TO 5

| | |
| --- | --- |
| 1 | Combined region of the inflow and offtake part of the dividing wall column |
| 2 | Enrichment section of the inflow part |
| 3 | Stripping section of the offtake part |
| 4 | Stripping section of the inflow part |
| 5 | Enrichment section of the offtake part |
| 6 | Combined region of the inflow and offtake part |
| 7 | Dividing wall |
| Z | Feed |
| L | Low-boiling fraction (methanol) |
| M | Intermediate boilers (1-methoxy-2-propanol and 2-methoxy-1-propanol as azeotrope with water) |
| S | High boilers |
| K | Condenser |
| V | Vaporizer |
| d | Vapor |
| f | Liquid |

Horizontal and diagonal or indicated diagonal lines in the columns symbolize packing made up of random packing elements or ordered packing which may be present in the column.

We claim:

1. A process for the continuously operated distillation purification of methanol, wherein the methanol is used as a solvent in a synthesis of propylene oxide by reaction of a hydroperoxide with propylene, wherein methoxypropanols formed as by-products from the reaction of the propylene oxide with the methanol are separated off simultaneously, wherein the solvent mixture obtained in the synthesis of the propylene oxide is separated in a dividing wall column into a low-boiling fraction comprising methanol, an intermediate-boiling fraction comprising the methoxypropanols as an azeotrope with water and a high-boiling fraction comprising water and propylene glycol, and
    wherein the propylene oxide is prepared by a process comprising at least (i) to (iii)
    (i) reacting the hydroperoxide with propylene to form a mixture,
    (ii) separating the unreacted hydroperoxide from the mixture resulting from (i),
    (iii) reacting the hydroperoxide which has been separated off in (ii) with propylene,
    wherein an isothermal fixed-bed reactor is used in (i), an adiabatic fixed-bed reactor is used in (iii), and a separation apparatus is used in (ii) and wherein hydrogen peroxide is used as hydroperoxide, and wherein the hydroperoxide and the propylene are reacted in the presence of a heterogeneous catalyst.

2. The process as claimed in claim 1, wherein the dividing wall column has from 15 to 60 theoretical plates.

3. The process as claimed in claim 1, wherein the distillation pressure is from 1 to 15 bar and the distillation temperature is from 30 to 140° C., in each case measured at the top of the column.

4. The process as claimed in claim 1, wherein the heterogeneous catalyst comprises the zeolite TS-1.

5. A process for the continuously operated distillation purification of methanol, wherein the methanol is used as a solvent in a synthesis of propylene oxide by reaction of a hydroperoxide with propylene, wherein methoxypropanols formed as by-products from the reaction of the propylene oxide with the methanol are separated off simultaneously, wherein the solvent mixture obtained in the synthesis of the propylene oxide is separated in a dividing wall column into a low-boiling fraction comprising methanol, an intermediate-boiling fraction comprising the methoxypropanols as an azeotrope with water and a high-boiling fraction comprising water and propylene glycol, and
    wherein the dividing wall column comprises and is configured as two thermally coupled columns,
    wherein the solvent mixture is separated into the low-boiling, intermediate-boiling and high-boiling fractions in a column downstream of a feed column, or
    the low-boiling and high-boiling fractions are taken off from the solvent mixture in the feed column and the intermediate-boiling fractions is taken off in the downstream column, or
    the high-boiling fraction is taken off from the solvent mixture in the feed column and the low-boiling and the intermediate-boiling fractions are taken off in downstream column, or
    the low-boiling fraction is taken off from the solvent mixture in the feed column and the intermediate-boiling and high-boiling fractions are taken off in the downstream column.

6. The process as claimed in claim 5, wherein the liquid stream taken from the bottom of one of the coupled columns is partly or completely vaporized before it is passed to the other column, and the gaseous stream taken off at the top of one of the coupled columns is partly or completely condensed before it is passed to the other column.

7. The process as claimed in claim 5, wherein the stream taken from the bottom of one of the coupled columns is partly or completely vaporized before it is passed to the other column, or the stream taken off at the top of one of the coupled columns is partly or completely condensed before it is passed to the other column.

8. The process as claimed in claim 5, wherein the propylene oxide is prepared by a process comprising at least (i) to (iii)
    (i) reacting the hydroperoxide with the propylene to form a mixture,
    (ii) separating the unreacted hydroperoxide from the mixture resulting from (i),
    (iii) reacting the hydroperoxide which has been separated off in (ii) with propylene,
    wherein an isothermal fixed-bed reactor is used in (i), an adiabatic fixed-bed reactor is used in (iii), and a separation apparatus is used in (ii) and wherein hydrogen peroxide is used as hydroperoxide, and wherein the hydroperoxide and the propylene are reacted in the presence of a heterogeneous catalyst.

9. The process as claimed in claim 8, wherein the heterogeneous catalyst comprises the zeolite TS-1.

* * * * *